(12) United States Patent
Chubak (10) Patent No.: US 9,759,829 B2
(45) Date of Patent: Sep. 12, 2017

(54) SYSTEM AND METHOD FOR GEOPHYSICAL DATA COLLECTION

(71) Applicant: Glenn Dale Chubak, Saskatchewan (CA)

(72) Inventor: Glenn Dale Chubak, Saskatchewan (CA)

(*) Notice: Subject to any disclaimer, the term of this patent is extended or adjusted under 35 U.S.C. 154(b) by 197 days.

(21) Appl. No.: 14/634,776

(22) Filed: Feb. 28, 2015

(65) Prior Publication Data

US 2016/0252640 A1    Sep. 1, 2016

(51) Int. Cl.
*G01V 3/02*    (2006.01)
*C12Q 1/00*    (2006.01)
*E21B 44/00*    (2006.01)

(52) U.S. Cl.
CPC .............. *G01V 3/02* (2013.01); *C12Q 1/00* (2013.01); *C12Q 2304/00* (2013.01); *E21B 44/00* (2013.01)

(58) Field of Classification Search
CPC ......... C12Q 1/00; C12Q 2304/00; E21B 1/00; E21B 44/00; G01V 1/00; G01V 2200/00
See application file for complete search history.

(56) References Cited

U.S. PATENT DOCUMENTS

| | | | | |
|---|---|---|---|---|
| 2003/0173081 | A1* | 9/2003 | Vinegar | E21B 43/243 166/272.1 |
| 2006/0238200 | A1* | 10/2006 | Johnstad | G01V 1/201 324/337 |
| 2010/0302902 | A1* | 12/2010 | Nance | G01V 1/133 367/21 |
| 2012/0232797 | A1* | 9/2012 | Frenkel | G01V 3/06 702/2 |
| 2013/0162255 | A1* | 6/2013 | Sudow | G01V 3/083 324/332 |
| 2014/0365246 | A1* | 12/2014 | Hayward | G06Q 40/08 705/4 |

\* cited by examiner

*Primary Examiner* — Jermele M Hollington
*Assistant Examiner* — Temilade Rhodes-Vivour
(74) *Attorney, Agent, or Firm* — Olive Law Group, PLLC (57) ABSTRACT

A system and method for geophysical data collection, for use with resistivity and induced polarization. The system and method include the use of a single voltage reference wire to which all voltage recorders or nodes are connected by means of a piercing wire connector, the voltage recorders providing a measurement of the potential voltage between the reference wire and the ground and allowing for calculation of relative voltage potentials between adjacent recorders.

18 Claims, 5 Drawing Sheets

SYSTEM AND METHOD FOR GEOPHYSICAL DATA COLLECTION

FIELD OF THE INVENTION

The present invention relates to systems and methods of geophysical surveying, and specifically to systems and methods for gathering or collecting geophysical data useful for resistivity or induced polarization data analysis techniques.

BACKGROUND OF THE INVENTION

It is well known in the art of geophysical surveying that analysis of resistivity and induced polarization data can provide useful information regarding subsurface structures and materials, including the possible presence of mineralization commonly associated with commercially valuable ore bodies. When electrical current is applied to the ground, variations in the subsurface can impact current flow and affect the distribution of electric potential, such that measurement of potential at the surface can provide information regarding the subsurface.

Conventional practice involves the use of a first pair of spaced-apart electrodes to pass current into the ground, and the resulting potential drop between a second pair of electrodes is measured. Resistivity and induced polarization effects have been used for many years to interpret the subsurface.

Figure 1A:
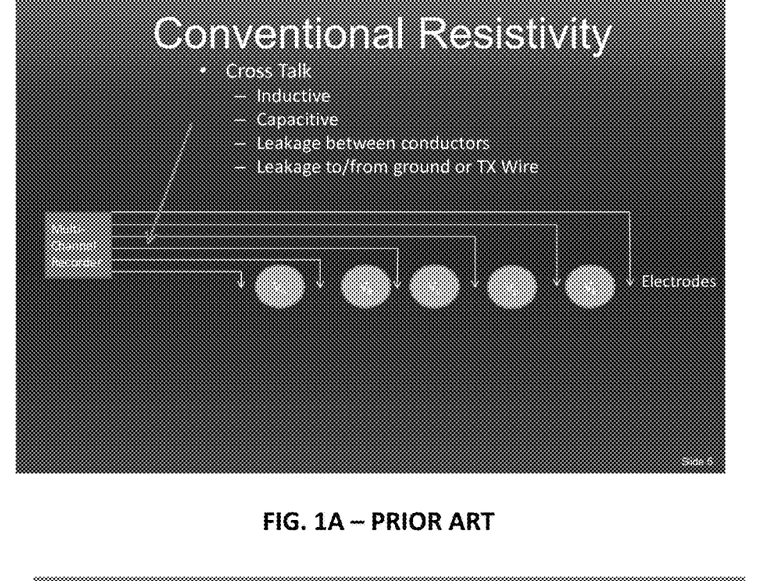
FIG. 1a is a simplified view of a prior art system using a single multi-channel recorder.
Figure 1B:
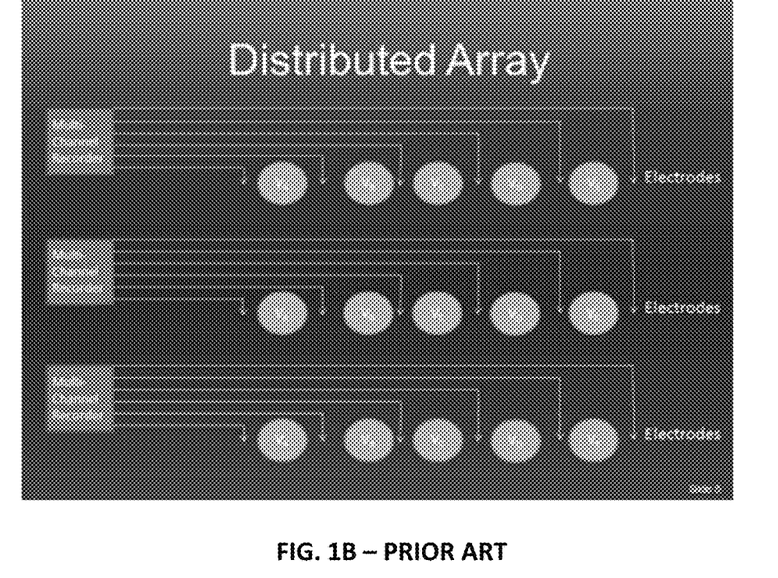
FIG. 1b is a simplified view of a prior art system using a distributed array of multi-channel recorders.

Early systems employed an analogue meter measuring a first dipole while current was transmitted into the ground using a second dipole, with data being transcribed by hand. Digital equipment became available in the 1980s and voltage data could thus be subjected to digitization and recorded to storage media. In a significant development, multi-channel measurement instruments allowed for simultaneous measurement of multiple dipoles (see FIG. 1a), and ultimately the practice moved to the use of multiple multi-channel measurement instruments in what is commonly referred to as a distributed array (see FIG. 1b).

While each development within the art increased the amount of data that could be collected and used for surveying purposes, the increased complexity dramatically increased the number of wires, the number of electrical connections, the setup complexity, and the size of the crew required to implement the system. As many exploration survey activities take place in relatively remote locales with restricted access and mobility within the areas, increases in complexity, equipment and crew sizes results in substantial cost increases and increased potential for crew injury.

In addition, one of the primary sources of noise in resistivity and induced polarization surveys is what is commonly known as "cross talk". Cross talk occurs where a signal from one conductor wire in the system interferes with the signal in an adjacent wire through inductive, capacitive or galvanic means. For example, signals from a current wire (part of the current transmission subsystem) may interfere with signals in the potential wire (part of the data collection subsystem). This problem is exacerbated as the systems become more complex and increase the number of wires employed for signal transmission.

What is needed, therefore, is a system and method for collecting geophysical data that reduces complexity and measurement noise.

SUMMARY OF THE INVENTION

The present invention therefore seeks to provide a system and method for geophysical data collection wherein a single conductor wire is used to obtain voltage potential data from a plurality of dipoles.

According to a first broad aspect of the present invention there is provided a system for use in gathering geophysical data derived from resistivity or induced polarization, the system comprising:
  a current transmitter for transmitting current into the ground in an area of interest;
  a single voltage reference wire for extension within the area of interest;
  a plurality of voltage recorders (also called nodes) spaced apart at respective measurement points along the length of and adjacent to the reference wire;
  each of the voltage recorders electrically connected to:
    a ground-engaging local electrode; and
    a wire connector; and
  each of the wire connectors for connecting to the reference wire adjacent the respective voltage recorder;
  wherein the voltage recorders are configured to measure the potential voltage between the reference wire and the ground at the respective measurement points.

In some exemplary embodiments of the first aspect, the current transmitter comprises two electrodes. The voltage recorders preferably record and store information for the potential voltage between the reference wire and the ground. Exemplary systems preferably further comprise remote information storage means, wherein each of the voltage recorders transmits information for the potential voltage between the reference wire and the ground to the remote information storage means.

Preferably one of the plurality of voltage recorders is used as a shorted node, with voltage measurements made between the shorted node and each of the local electrodes for the other voltage recorders.

Exemplary systems preferably comprise a remote computer station, the remote computer station configured to allow selection of the voltage recorder to use as the shorted node. The remote computer station is preferably in wireless communication with each of the voltage recorders for receiving information for the potential voltage between the reference wire and the ground. The local electrodes are preferably metal stakes configured to be driven into the ground, and the wire connector is preferably configured to pierce a coating of the reference wire to establish an electrical connection.

The reference wire may be deployed linearly across the area of interest, or in a non-linear pattern across the area of interest to create a two-dimensional grid of measurement points.

In some embodiments each of the voltage recorders is GPS-enabled to provide locational information for each of the voltage recorders.

Where the exemplary system comprises a remote computer station, each of the voltage recorders preferably comprises:
  voltage recording means;
  on-off controls for the voltage recording means;
  information storage means for storing voltage information;
  a microprocessor for calculating an on-time average voltage when the current transmitter is transmitting current to the ground, and an off-time average voltage when the current transmitter is not transmitting current to the ground;

GPS functionality to determine a location of the voltage recorder; and a transceiver for:
transmitting voltage information, on-time average voltage, off-time average voltage and GPS information to the remote computer station; and
receiving control signals for the on-off controls.

Where one of the plurality of voltage recorders is used as a shorted node, with voltage measurements made between the shorted node and each of the local electrodes for the other voltage recorders, the transceiver may be used to allow the remote computer station to select which of the voltage recorders will be the shorted node.

According to a second broad aspect of the present invention there is provided a method for gathering geophysical data derived from resistivity or induced polarization, the method comprising the steps of:

a. positioning a single voltage reference wire within an area of interest;
b. positioning a plurality of voltage recorders in spaced-apart arrangement along the reference wire, each of the voltage recorders electrically connected to a local electrode and a wire connector;
c. connecting each of the local electrodes to the ground;
d. connecting each of the wire connectors to the reference wire;
e. shorting one of the voltage recorders;
f. transmitting current into the ground in the area of interest;
g. beginning recording potential voltages between the reference wire and the ground at each of the voltage recorders;
h. turning the current transmission off and on at least one time; and
i. ceasing recording potential voltages between the reference wire and the ground at each of the voltage recorders.

In some exemplary embodiments of the second aspect, the step of positioning the reference wire comprises extending the reference wire in a substantially straight line across the area of interest. This step may alternatively comprise positioning the reference wire in a non-linear pattern across the area of interest to create a grid arrangement of the voltage recorders.

Some exemplary methods further comprise:
storing the recorded potential voltages in the voltage recorders;
calculating average on-time potential voltage figures for each period during which the current is transmitted into the ground, and storing the average on-time potential voltage figures;
calculating average off-time potential voltage figures for each period during which the current is not transmitted into the ground, and storing the average off-time potential voltage figures; and
determining a voltage recorder location using global positioning means, and storing the voltage recorder location.

Where the above is the case, the exemplary method may further comprise transmitting the potential voltages, the average on-time potential voltage figures, the average off-time potential voltage figures and the voltage recorder location to a remote computer station.

The step of shorting one of the voltage recorders preferably comprises allowing electrical connection between the reference wire and the ground through the voltage recorder.

Two electrodes are preferably used for the step of transmitting current into the ground in the area of interest.

A detailed description of an exemplary embodiment of the present invention is given in the following. It is to be understood, however, that the invention is not to be construed as being limited to this embodiment. The exemplary embodiment is directed to a particular application of the present invention, while it will be clear to those skilled in the art that the present invention has applicability beyond the exemplary embodiment set forth herein.

BRIEF DESCRIPTION OF THE DRAWINGS

In the accompanying drawings, which illustrate an exemplary embodiment of the present invention.

An exemplary embodiment of the present invention will now be described with reference to the accompanying drawings.

DETAILED DESCRIPTION OF EXEMPLARY EMBODIMENT

Throughout the following description specific details are set forth in order to provide a more thorough understanding to persons skilled in the art. However, well known elements may not have been shown or described in detail to avoid unnecessarily obscuring the disclosure. The following description of examples of the invention is not intended to be exhaustive or to limit the invention to the precise forms of any exemplary embodiment. Accordingly, the description and drawings are to be regarded in an illustrative, rather than a restrictive, sense.

Turning now to FIGS. 2a, 2b, 3, 4a and 4b, an exemplary embodiment of the present invention is illustrated. The exemplary system comprises a current transmitter, a single voltage reference wire, a plurality of nodes (only six are shown, the reduced number merely for illustration) positioned along the length of the reference wire, and a remote computer station for controlling the system. The current transmitter can be a conventional two electrode arrangement, and is used to transmit current into the ground near the reference wire.

Figure 2A:
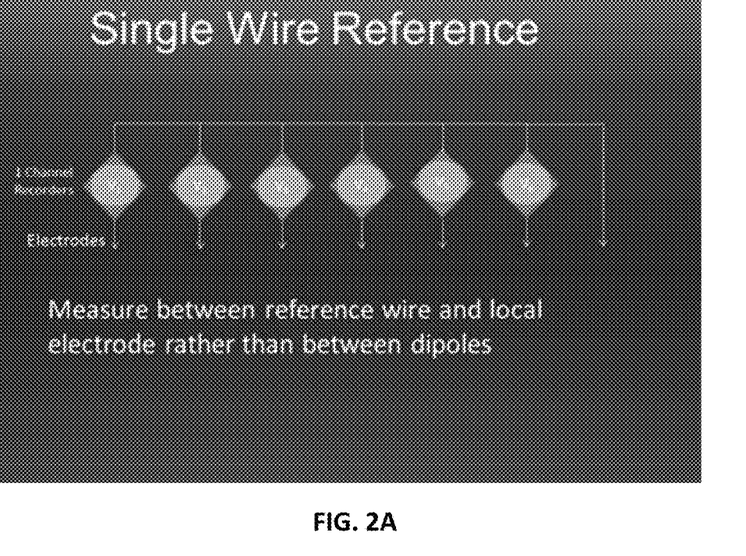
FIG. 2a is a simplified view of an exemplary system according to the present invention.

FIG. 2a is a simplified diagram showing a single reference wire in accordance with the present invention. The reference wire may be deployed linearly across the area of interest, or in a non-linear pattern across the area of interest to create a two-dimensional grid of measurement points. For example, the reference wire can be stretched out so that it is substantially a straight line; alternatively, the reference wire could be placed on the ground in an irregular or zig-zag pattern to allow the recorders to be positioned in a two-dimensional surface grid pattern (but still with only a single reference wire).

Instead of the prior art multi-channel recorders, the exemplary embodiment employs a series of single-channel recorders. The term "recorder" may be replaced with the equivalent term "node" herein.

Unlike prior art systems that employ substantial numbers of wires to connect various components, the exemplary embodiment has a single reference wire, with all of the recorders electrically connected between the reference wire and the ground. This reduction of wire alone makes the present invention potentially simpler and quicker to set up. There is no particular reference wire type and gauge that can be established for every possible application, as this would vary from one context to the next, as would be clear to those skilled in the art.

Figure 3:
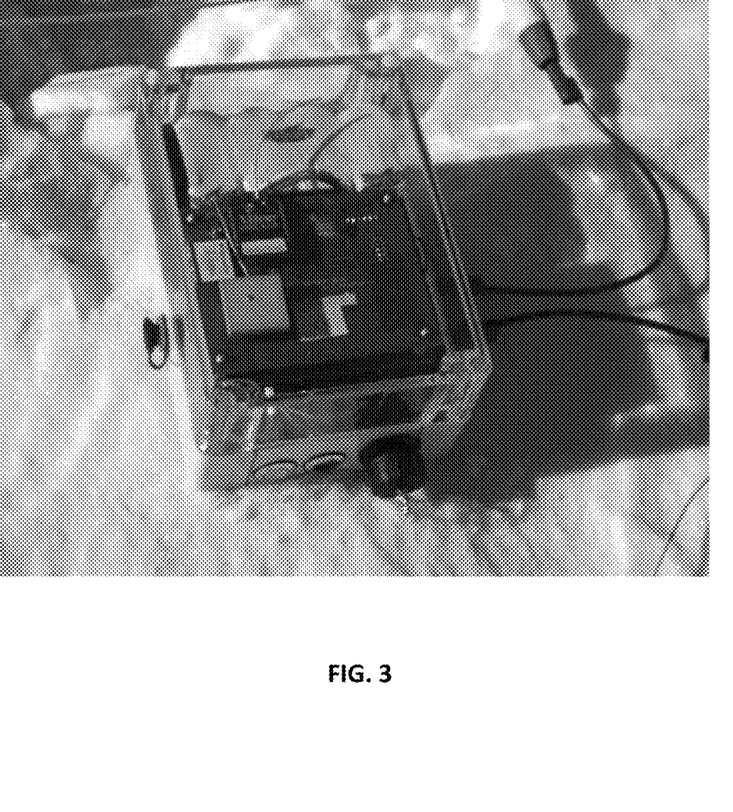
FIG. 3 is a photograph of a prototype voltage recorder connected to the single reference wire.

FIG. 3 shows a photograph of an exemplary node. Each node is connected by means of a local electrode to the ground, and connected by means of an insulation piercing wire connector to the single reference wire. The local electrode is a metal stake in the exemplary embodiment, and it is driven into the ground. The piercing wire connector, which can be seen in FIG. 3, is a commercially available component that penetrates the coating of the reference wire to enable an electrical connection between the reference wire and the node. By using a piercing wire connector, the exemplary embodiment avoids cutting the reference wire or making more complicated conventional electrical connections. The use of a piercing wire connector also reduces setup time considerably and reduces the need for specialized tools, while eliminating the need for knives and wire stripping reduces common safety risks.

One of the nodes along the reference wire will be selected as a shorted node. A shorted node is required in the exemplary embodiment to provide a fixed potential, as will be understood by those skilled in the art. Voltage measurements are made between the shorted node and each of the local electrodes for the other nodes. The shorted node will be internally shorted to establish an electrical connection between the reference wire and the ground. In the exemplary embodiment, the remote computer station is used to select which node will be the shorted node, and will wirelessly instruct the node to actuate the electrical connection between the reference wire and the ground by completing the circuit.

Figure 2B:
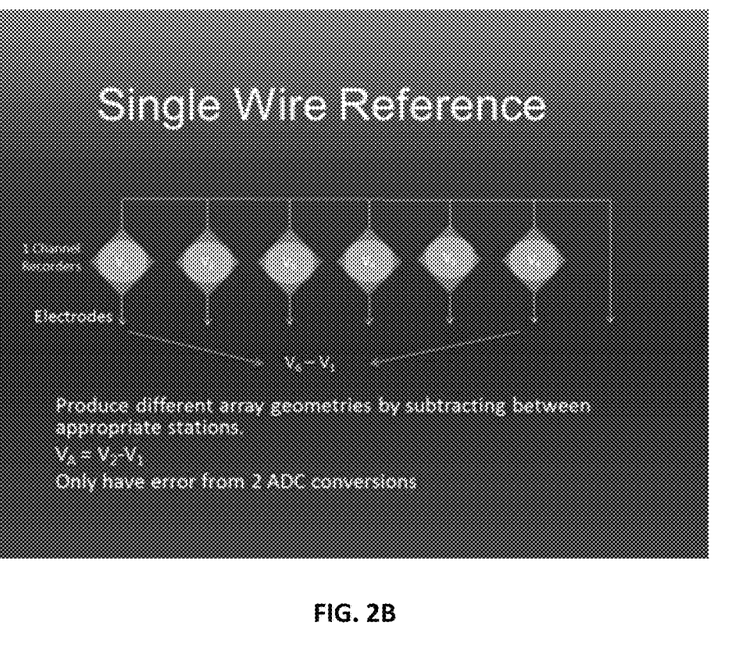
FIG. 2b is a simplified view of the exemplary system.

This allows voltage measurements to be made between the shorted node and each of the electrode positions along the reference wire. As stated in FIG. 2a, the exemplary system and method involve measuring between the reference wire and the local electrode that is connected to the node, rather than the conventional method wherein measurements are made between dipoles. Measurements between adjacent points can be calculated from the relative voltages of the two points, and thus voltage potentials can be calculated between any two points on the reference wire, as shown in FIG. 2b. Such a method would be theoretically possible with more conventional recording equipment arrangements, but it would require the summation of multiple dipoles which adds noise with each additional dipole used; in the present invention, any dipole can be calculated with the same system noise because only two measurements are being used in any particular calculation.

It is known that a greater distance between voltage recorders allows data on deeper subsurface conditions. Thus, as indicated in FIG. 2b, different "array geometries" or dipole spacing can generate different types and amounts of data, and thus selection of which dipoles to use for the calculation can provide different information. As only two nodes will be involved in a given calculation, noise is reduced as there will only be potential error from two arbitrary dipole calculation conversions.

Each node serves a number of purposes in the exemplary embodiment:
 selective (on-off) recording of data regarding the potential voltage between the reference wire and the ground at the location of the node
 storing the data
 transmitting the data by means of a wireless transceiver to the remote computer station
 calculating (through a microprocessor) an "on-time" average voltage when the current transmitter is transmitting current to the ground, and an "off-time" average voltage when the current transmitter is not transmitting current to the ground; and
 using GPS functionality to determine and transmit the location of the voltage recorder In the exemplary embodiment, the system includes a remote computer station. One of the functions of the remote computer station is to communicate wirelessly with the nodes to turn the data recording on and off. In a preferred method, recording would be turned on immediately after current has been transmitted into the ground, and would continue through a desired number of on-off cycles of current transmission.

The voltage recorders are configured to measure the potential voltage between the reference wire and the ground at the respective measurement points. During the recording period when the current transmission is stopped, or the "off-time" in conventional terminology (when induced polarization effects would be noted), each recorder records the voltage readings; also, at the end of the off-time period, the recorder (through the microprocessor) will calculate an average voltage during the off-time, which is referred to as Vs (or Voltage-Secondary). Similarly, during the recording period when the current transmission is active, or the "on-time" in conventional terminology (when resistivity effects would be noted), each recorder records the voltage readings; at the end of the on-time period the recorder (through the microprocessor) will calculate an average voltage during the on-time, which is referred to as Vp (or Voltage-Primary). The values for Vp and Vs are also wirelessly transmitted to the remote computer station in the exemplary embodiment, and these can be used for resistivity (Vp) and induced polarization (Vs) analyses.

As indicated above, conventional systems experience challenges from cross talk, which occurs where a signal from one conductor wire (for example, a potential wire such as the reference wire) in the system interferes with the signal in an adjacent wire (for example, the current wire used for current transmission) through inductive, capacitive or galvanic means. The single reference wire system of the present invention is inherently insensitive to cross talk between potential wires as there is only one potential wire (i.e. the reference wire). Cross talk between the current wire and the reference wire in the exemplary embodiment is effectively cancelled as the nodes are sampling the voltage simultaneously and the final voltage across the dipole (Va) is calculated by $$Va=(V1-Vr)-(V2-Vr)$$

where:
 $V1$=voltage at node 1 relative to the reference wire
 $Va$=voltage across dipole a
 $V2$=voltage at node 2 relative to the reference wire
 $Vr$=voltage on the reference wire relative to infinity
 This can be rearranged to $$Va = V1 - V2 - Vr + Vr$$

which reduces to $$Va = V1 - V2$$

Since Vr cancels, it is shown that the actual potential on Vr is not significant and hence potentials induced on the wire are cancelled.

Another potential noise source with the single wire reference design is voltage potential changes along the wire. However, since the wire is only grounded in one location by the shorted node, it can be assumed to a first order approximation that no current is flowing in the wire. The voltage drop over the length of the wire is given by $$V = IR$$

where V is the voltage drop, I is the current in the wire and R is the resistance of the wire.

Since I is approaching 0 due to only having a single grounding point, the voltage drop on the wire will be very small at sub radio frequencies.

To effectively manage the nodes while deployed, a wireless "mesh" network is used. Telemetry information such as battery level, system health and internal node temperature is relayed to the remote computer station. Internal node temperature can be an important factor, as it can affect battery health and data accuracy. During the data acquisition, the voltage measurements are relayed to the remote computer station to ensure validity of the data. In some cases, wire connections can become inoperative during the course of a survey due to weather or wildlife and without real time data, the data quality can be compromised. The wireless network is also useful for controlling the shorted node during acquisition. During acquisition, an average of the on-time voltage and an average of the off-time voltage from the square wave is transmitted back to the remote computer station, and this data can be used to monitor data quality and make adjustments to the survey speed.

In operation, a method according to this exemplary embodiment would begin with positioning a single voltage reference wire within an area of interest, then positioning a plurality of voltage recorders in spaced-apart arrangement along the reference wire, each of the voltage recorders electrically connected to a local electrode and a wire connector. The reference wire may be laid out in a linear pattern, or in a non-linear pattern to create a grid arrangement of the voltage recorders. The local electrodes would then be connected to the ground, and the wire connectors would be connected to the reference wire.

One of the voltage recorders would be shorted using the remote computer station, and the operator would commence current transmission into the ground. Recording of potential voltages between the reference wire and the ground at each of the voltage recorders would then be initiated. At various points during the survey, and while recording continued, the current transmission would be turned off and on. Finally, the recording of potential voltages would be terminated.

During data acquisition, each node would store the recorded potential voltages, and would also calculate both average on-time potential voltage figures for each period during which the current is transmitted into the ground, and average off-time potential voltage figures for each period during which the current is not transmitted into the ground. The exemplary method includes transmitting the potential voltages, the average on-time potential voltage figures, the average off-time potential voltage figures and the voltage recorder location (derived from each node's GPS functionality) to the remote computer station.

Figure 4A:
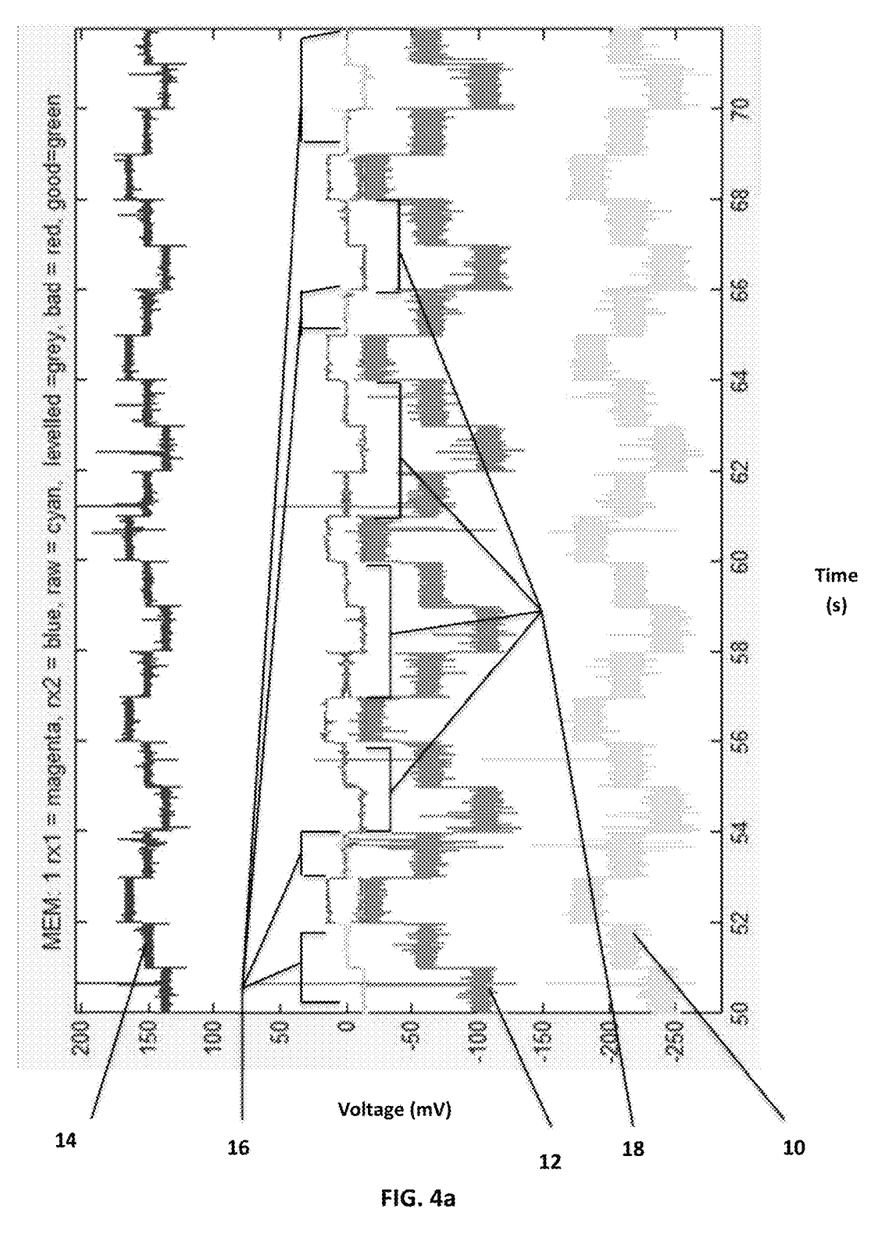
FIGS. 4a and 4b provide a chart illustrating geophysical data received using an embodiment of the present invention.
Figure 4B:
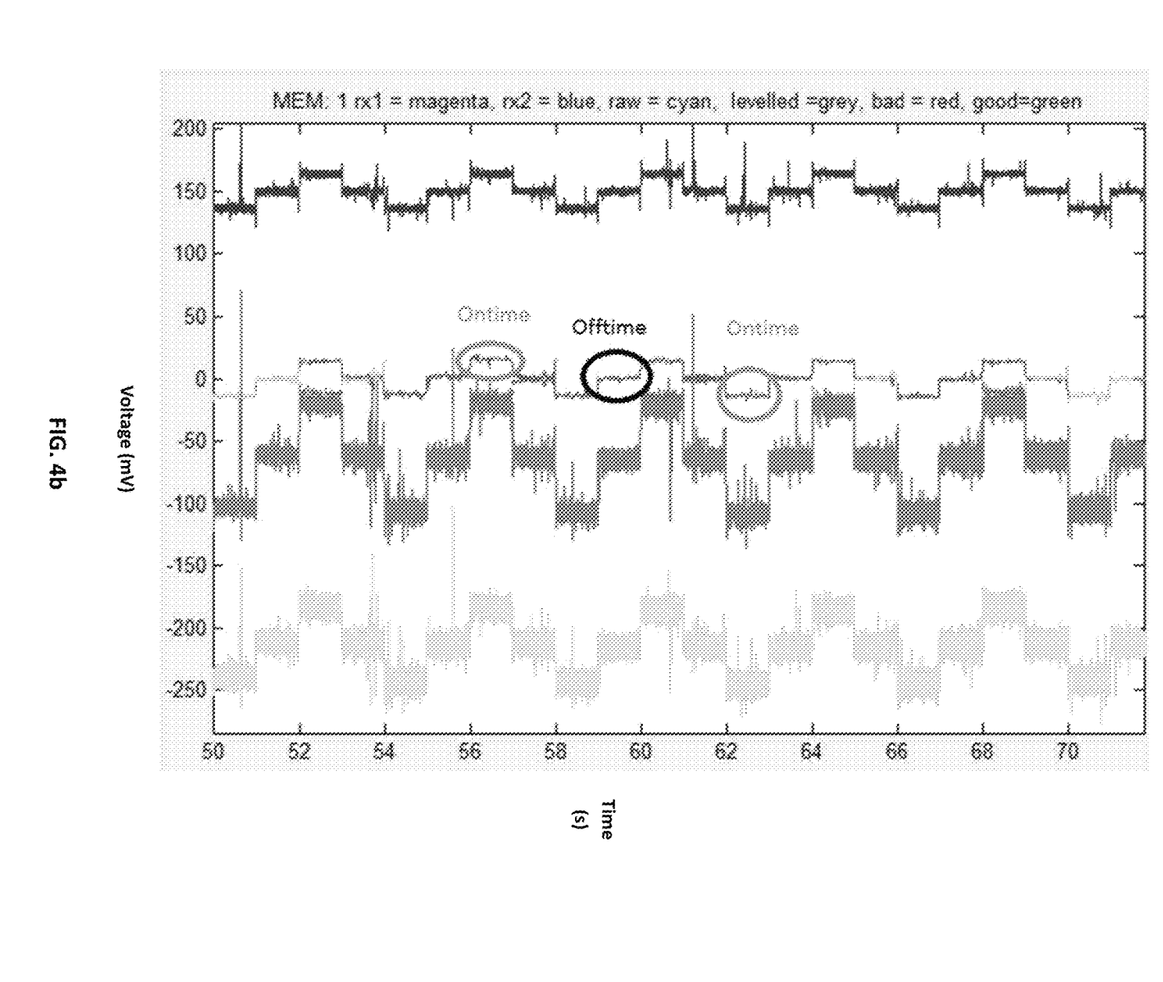

FIG. 4a is a chart illustrating a plot of voltage readings from a single recorder over a period of time, which can then be used in further processing and analysis. Voltage in millivolts (mV) is plotted on the vertical axis, with time in seconds (s) plotted on the horizontal axis. Line 10 represents a signal V1 received from the recorder, while line 12 represents a signal V2 received from the recorder. The top line 14 shows the resultant signal Va obtained by subtracting V1 from V2. The DC offset is subtracted from Va and the signal is broken into segments shown in the plot immediately above the line 12. Each cycle is then flipped so it is positive polarity. Overlaid on the plot above line 12 are cycles 18 that are discarded due to noise, and cycles 16 that are retained and used in further processing. The signal shown in FIGS. 4a and 4b is called a bi-polar square wave. As can be seen in FIG. 4b, it illustrates a positive on-time value followed by an off-time, followed by a negative on-time value followed by another off-time; the series then repeats.

There are thus numerous advantages to the present invention when compared to the prior art. For example, the use of a single reference wire to which all recorders are connected results in significantly reduced equipment complexity, which also means that a reduced crew size will be necessary. Cost savings can be realized, while still having a system that is flexible in application. Issues with system noise including "cross talk" can be addressed, while the system itself can potentially be scaled up to hundreds of nodes.

As will be clear from the above, those skilled in the art would be readily able to determine obvious variants and functional equivalents capable of providing the stated functionality, and all such variants and functional equivalents are intended to fall within the scope of the present invention.

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to".

"connected", "coupled", or any variant thereof, means any connection or coupling, either direct or indirect, between two or more elements; the coupling or connection between the elements can be physical, logical, or a combination thereof.

"herein", "above", "below", and words of similar import, when used to describe this specification shall refer to this specification as a whole and not to any particular portions of this specification.

"or", in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to herein, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of methods and apparatus have been described herein for purposes of illustration. These are only examples. The technology provided herein can be applied to contexts other than the exemplary contexts described above. Many alterations, modifications, additions, omissions and permutations are possible within the practice of this invention. This invention includes variations on described embodiments that would be apparent to the skilled person, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

The foregoing is considered as illustrative only of the principles of the invention. The scope of the claims should not be limited by the exemplary embodiment set forth in the foregoing, but should be given the broadest interpretation consistent with the specification as a whole.

The invention claimed is:

1. A system for use in gathering geophysical data derived from resistivity or induced polarization, the system comprising:
    a current transmitter for transmitting current into the ground in an area of interest;
    a single voltage reference wire for extension within the area of interest;
    a plurality of voltage recorders spaced apart at respective measurement points along the length of and adjacent to the reference wire;
    each of the voltage recorders electrically connected to:
        a ground-engaging local electrode; and
        a wire connector; and
    each of the wire connectors for connecting to the reference wire adjacent the respective voltage recorder;
    wherein the voltage recorders are configured to measure the potential voltage between the reference wire and the ground at the respective measurement points;
    wherein each of the voltage recorders comprises:
        voltage recording means;
        on-off controls for the voltage recording means;
        information storage means for storing voltage information;
        a microprocessor for calculating an on-time average voltage when the current transmitter is transmitting current to the ground, and an off-time average voltage when the current transmitter is not transmitting current to the ground;
        GPS functionality to determine a location of the voltage recorder; and
        a transceiver for:
            transmitting voltage information, on-time average voltage, off-time average voltage and GPS information to the remote computer station; and
            receiving control signals for the on-off controls.

2. The system of claim 1 wherein the current transmitter comprises two electrodes.

3. The system of claim 1 wherein each of the voltage recorders records and stores information for the potential voltage between the reference wire and the ground.

4. The system of claim 1 further comprising remote information storage means, wherein each of the voltage recorders transmits information for the potential voltage between the reference wire and the ground to the remote information storage means.

5. The system of claim 1 wherein one of the plurality of voltage recorders is used as a shorted node, with voltage measurements made between the shorted node and each of the local electrodes for the other voltage recorders.

6. The system of claim 5 further comprising a remote computer station, the remote computer station configured to allow selection of the voltage recorder to use as the shorted node.

7. The system of claim 1 wherein the local electrodes are metal stakes configured to be driven into the ground.

8. The system of claim 1 wherein the wire connector is configured to pierce a coating of the reference wire to establish an electrical connection.

9. The system of claim 1 wherein the reference wire is deployed in a non-linear pattern across the area of interest to create a two-dimensional grid of measurement points.

10. The system of claim 1 further comprising a remote computer station in wireless communication with each of the voltage recorders for receiving information for the potential voltage between the reference wire and the ground.

11. The system of claim 1 wherein each of the voltage recorders is GPS-enabled to provide locational information for each of the voltage recorders.

12. The system of claim 1 wherein one of the plurality of voltage recorders is used as a shorted node, with voltage measurements made between the shorted node and each of the local electrodes for the other voltage recorders, and the transceiver is used to allow the remote computer station to select which of the voltage recorders will be the shorted node.

13. A method for gathering geophysical data derived from resistivity or induced polarization, the method comprising the steps of:
    a. positioning a single voltage reference wire within an area of interest;
    b. positioning a plurality of voltage recorders in spaced-apart arrangement along the reference wire, each of the voltage recorders electrically connected to a local electrode and a wire connector;
    c. connecting each of the local electrodes to the ground;
    d. connecting each of the wire connectors to the reference wire;
    e. shorting one of the voltage recorders;
    f. transmitting current into the ground in the area of interest;
    g. beginning recording potential voltages between the reference wire and the ground at each of the voltage recorders;
    h. turning the current transmission on and off at least one time;
    i. ceasing recording potential voltages between the reference wire and the ground at each of the voltage recorders;
    j. storing the recorded potential voltages in the voltage recorders;
    k. calculating average on-time potential voltage figures for each period during which the current is transmitted into the ground, and storing the average on-time potential voltage figures;

l. calculating average off-time potential voltage figures for each period during which the current is not transmitted into the ground, and storing the average off-time potential voltage figures; and m. determining a voltage recorder location using global positioning means, and storing the voltage recorder location.

14. The method of claim 13 wherein the step of positioning the reference wire comprises extending the reference wire in a substantially straight line across the area of interest.

15. The method of claim 13 wherein the step of positioning the reference wire comprises positioning the reference wire in a non-linear pattern across the area of interest to create a grid arrangement of the voltage recorders.

16. The method of claim 13 comprising transmitting the potential voltages, the average on-time potential voltage figures, the average off-time potential voltage figures and the voltage recorder location to a remote computer station.

17. The method of claim 13 wherein the step of shorting one of the voltage recorders comprises allowing electrical connection between the reference wire and the ground through the voltage recorder.

18. The method of claim 13 wherein two electrodes are used for the step of transmitting current into the ground in the area of interest.

* * * * *